(12) United States Patent
Brand et al.

(10) Patent No.: US 8,511,141 B2
(45) Date of Patent: Aug. 20, 2013

(54) STACK GAS MEASUREMENT DEVICE AND METHOD THEREFOR

(75) Inventors: Joel A. Brand, Colorado Springs, CO (US); Aron D. Gaus, Cedar Park, TX (US)

(73) Assignee: Brand-Gaus, LLC, Cedar Park, TX (US)

( * ) Notice: Subject to any disclaimer, the term of this patent is extended or adjusted under 35 U.S.C. 154(b) by 724 days.

(21) Appl. No.: 12/646,484

(22) Filed: Dec. 23, 2009

(65) Prior Publication Data
US 2011/0146378 A1    Jun. 23, 2011

(51) Int. Cl.
*G01N 7/00* (2006.01)

(52) U.S. Cl.
USPC ....................................................... 73/23.31

(58) Field of Classification Search
USPC ....................................................... 73/23.31
See application file for complete search history.

(56) References Cited

U.S. PATENT DOCUMENTS

| | | | | |
|---|---|---|---|---|
| 3,528,779 A | * | 9/1970 | Fontijn | 436/135 |
| 3,882,028 A | * | 5/1975 | Zolner | 250/361 C |
| 3,963,928 A | * | 6/1976 | Zolner | 250/361 C |
| 4,775,633 A | * | 10/1988 | Rounbehler | 436/106 |
| 4,974,453 A | | 12/1990 | Hohorst | |
| 5,219,534 A | * | 6/1993 | Reynolds | 422/186.3 |
| 5,916,523 A | | 6/1999 | Yan et al. | |
| 6,112,574 A | | 9/2000 | Hirano et al. | |
| 6,143,245 A | * | 11/2000 | Yan et al. | 422/52 |
| 6,418,957 B1 | | 7/2002 | Goodyear | |
| 6,886,396 B2 | | 5/2005 | Tsukamoto et al. | |
| 7,021,130 B2 | | 4/2006 | Schmidt | |
| 7,059,205 B1 | | 6/2006 | Weaver | |
| 7,520,155 B2 | | 4/2009 | Sasaki et al. | |
| 2001/0049973 A1 | | 12/2001 | Hanashiro et al. | |
| 2002/0156568 A1 | | 10/2002 | Knott et al. | |
| 2003/0136177 A1 | | 7/2003 | Hendren et al. | |
| 2004/0226354 A1 | | 11/2004 | Schmidt | |
| 2006/0236752 A1 | | 10/2006 | Nakamura | |
| 2008/0190168 A1 | | 8/2008 | Booker et al. | |

FOREIGN PATENT DOCUMENTS

JP    09049787 A    2/1997

* cited by examiner

*Primary Examiner* — Hezron E Williams
*Assistant Examiner* — Mark A Shabman
(74) *Attorney, Agent, or Firm* — Larson Newman, LLP

(57) ABSTRACT

A gas sampling device includes an analysis block defining a first portion of a chamber and a dilution block defining a second portion of the chamber. The sampling device includes an exhaust gas orifice at the first portion for withdrawing gas from the chamber in response to an applied suction, a sample gas orifice at the second portion to modify passage of a sample gas entering the chamber in response to the suction, and a dilution gas orifice at the second portion to modify passage of a dilution gas entering the chamber in response to the suction.

16 Claims, 4 Drawing Sheets

STACK GAS MEASUREMENT DEVICE AND METHOD THEREFOR

FIELD OF THE DISCLOSURE

The present disclosure relates generally to measuring and testing devices, and relates more particularly to devices for measuring stack gases in the exhaust of combustion sources.

BACKGROUND

Internal combustion engines, boilers, power generation equipment, and equipment that burn a fuel typically produce exhaust or stack emissions that can include byproducts such as nitrogen oxides and sulfur oxides. Government regulations may require that sources of these byproducts include a device to monitor the quantity or concentration of particular gases that are emitted during operation. Real-time measurement of these byproducts can also be used by closed-loop control systems to regulate the operation of an engine or other combustion system. Monitoring devices can generally be classified into one of three fundamental types based on how the exhaust or emission is sampled, including in-situ, extractive, and dilution extractive.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

The numerous innovative teachings of the present application will be described with particular reference to the presently preferred exemplary embodiments. However, it should be understood that this class of embodiments provides only a few examples of the many advantageous uses of the innovative teachings herein. In general, statements made in the specification of the present application do not necessarily limit any of the various claimed inventions. Moreover, some statements may apply to some inventive features but not to others.

Figure 1:
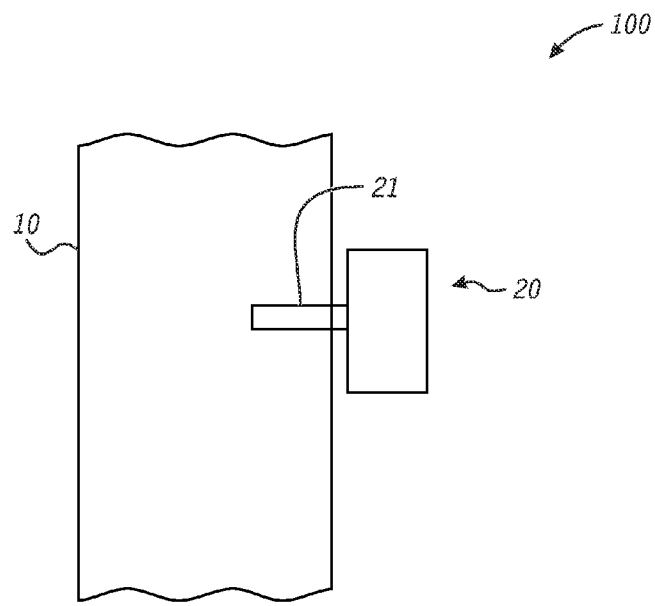
FIG. 1 is a block diagram illustrating a monitoring device attached to an exhaust conduit in accordance with a specific embodiment of the present disclosure.

FIG. 1 shows a monitoring device 20 attached to an exhaust conduit 10 in accordance with a specific embodiment of the present disclosure. Monitoring device 20 includes a sample probe 21. Exhaust conduit 10 can include an exhaust pipe or duct for transmitting exhaust gases produced by an internal combustion engine, a stack for expelling exhaust combustion products from a burner, or another type of conduit for containing the passage of an exhaust gas. In an embodiment, monitoring device 20 can be closely coupled to exhaust conduit 10. Sample probe 21 supports passage of a portion of the exhaust gas stream (sample gas) present within the exhaust conduit into monitoring device 20. Monitoring device 20 may include electronic instrumentation devices, or electrical signals produced at monitoring device 20 can be conducted to electronic instrumentation external to monitoring device 20 via signal wiring (not shown at FIG. 1). For the purpose of example, the present disclosure is described in the context of a nitric oxide gas monitoring device using a detector based on chemiluminescence analysis, but devices and methods disclosed herein can be employed to sample and monitor other gases and may conduct analysis using another type of detector.

Monitoring device 20 operates based on a dilution-extraction process whereby a sample gas received via probe 22 is diluted with another gas, such as air or nitrogen. Dilution of the sample gas is carried out in proximity to the exhaust conduit thereby substantially eliminating the need to transport undiluted sample gas. The sample gas is diluted to reduce the dew point of the resulting stream of diluted sample gas and thus to reduce condensation of moisture within monitoring device 20. Additionally, dilution of the sample gas can improve the accuracy of monitoring device 20 by reducing the concentration of water, carbon dioxide, acids, and other chemicals and gases present in the diluted sample that can interfere with analysis of the sample gas. Because the concentration of nitric oxide is reduced by the dilution process, the accuracy of monitoring device 20 is determined, in part, by the accuracy at which a stable dilution ratio is maintained. The operation of monitoring device 20 can be better understood with reference to FIGS. 2-6.

Figure 2:
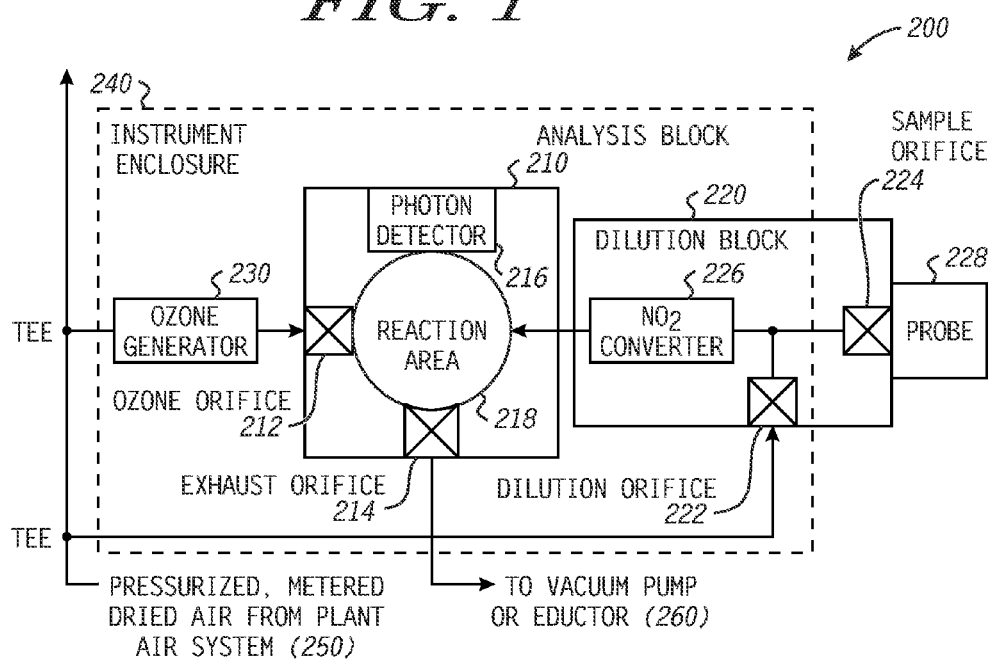
FIG. 2 is schematic block diagram illustrating an example implementation of the monitoring device of FIG. 1 in accordance with a specific embodiment of the present disclosure.

FIG. 2 shows a monitoring device 200 in accordance with a specific embodiment of the present disclosure. Monitoring device 200 is an example implementation of monitoring device 20 of FIG. 1 and includes an analysis block 210, a dilution block 220, and an ozone generator 230, included in an instrument enclosure 240. Analysis block 210 includes an ozone gas orifice 212, an exhaust gas orifice 214, a photon detector 216, and a reaction area 218. Dilution block 220 includes a dilution gas orifice 222, a sample gas orifice 224, a nitrogen dioxide ($NO_2$) converter 226, and a probe 228. Pressurized and metered dried air 250 is provided to ozone generator 230 and at dilution orifice 222. Suction 260 is applied at exhaust orifice 214. Analysis block 210 and dilution block 220 are housings joined together to provide an enclosed chamber that can be maintained at a substantially uniform barometric pressure. A portion of the chamber is defined within the analysis block and another portion of the chamber is defined within the dilution block. Ingress and egress of gases to and from the chamber is limited to that provided by the ozone gas orifice, the exhaust gas orifice, the dilution gas orifice, and the sample gas orifice. The analysis block and the dilution block can be constructed of metal, such as stainless steel or aluminum. One or more gaskets can be used to provide an air-tight seal at the interface(s) between the analysis block and the dilution block. The chamber includes reaction area 218 located within analysis block 210.

During operation, a vacuum pump, an eductor, or another suitable vacuum device (not shown at FIG. 2) provides suction at an outlet of analysis block 210 via exhaust gas orifice 214 causing sample gas, dilution gas, and ozone gas to be drawn into the chamber. A desired ratio (partial pressure) of ozone gas, dilution gas, and sample gas is maintained within the chamber by a relative degree of restriction provided by the ozone orifice, the dilution orifice, and the sample gas orifice, respectively. The combined flow of gases into and out of the chamber is further determined by a degree of restriction provided by exhaust gas orifice 214. Sample gas orifice 224 can be integrated with probe 228 thereby removing the necessity to transport undiluted sample gases within monitoring device 200. Probe 228 can include a filter device for substantially removing particulate matter.

During operation, probe 228 extracts a stream of sample gas from a stream of exhaust gases communicated by a stack or duct, such as exhaust conduit 10 of FIG. 1. The sample gas enters dilution block 220 via sample gas orifice 224 and is substantially immediately diluted with a dilution gas received at dilution block 220 via dilution gas orifice 222. As illustrated at FIG. 2, the dilution gas can be dried air that also is provided to ozone generator 230, or it can be another gas, such as nitrogen gas. The diluted sample gas enters analysis block 210 where it combines with ozone gas provided by ozone generator 230 via ozone orifice 212. NO gas present in the sample gas reacts with the ozone gas at reaction area 218 to form $NO_2$ in an excited state, which then radiatively decays, emitting photons in a process known as chemiluminescence. Photon detector 216 detects the emitted photons, and the number of photons detected by the photon detector is substantially proportional to the concentration of NO gas in the diluted sample gas. Thus, the rate of photon emissions occurring at reaction area 218 can be used to estimate the concentration of NO gas included in the diluted sample gas, and ultimately to estimate the concentration of NO gas included in the exhaust gas stream at exhaust conduit 10.

Ozone gas orifice 212, exhaust gas orifice 214, dilution gas orifice 222, and sample gas orifice 224 each include an internal bore diameter that is precision machined to restrict passage of a corresponding gas to a desired degree. The orifices can be manufactured from sapphire jewels or another suitable material. The bore diameter of an orifice typically ranges from approximately 4 mils to 25 mils (0.004-0.025 inches), however a larger or smaller bore diameter can be used without departing from the scope of the present disclosure. The ratio of each respective gas at reaction area 218 is determined by the ratio of the bore diameter of the corresponding orifice. In an embodiment, a preferred ratio of ozone gas/dilution gas/sample gas is 5/10/1 (5 parts ozone gas, 10 parts dilution gas, 1 part sample gas), however a dilution ratio (a ratio of dilution gas to sample gas) can range from approximately 1:1 to approximately 50:1, and is preferably approximately 10:1 to 20:1. The dilution ratio can be selected based on the chemical properties of the exhaust gases. The ratio of ozone gas to the diluted sample gas can range from approximately 1:10 to 1:1, and is preferably approximately 1:2. The bore diameter of exhaust gas orifice 214 determines the overall flow rate of the combined gases through monitoring device 200. In an embodiment, the rate of gas flow through monitoring device 200, and reaction area 218 in particular, is approximately 0.1 to 0.5 liters per minute.

It is often desirable to determine a combined concentration of both NO and $NO_2$ included in a sample gas, however only NO gas present in the sample takes part in the previously described reaction with the ozone gas. In order for monitoring device 200 to measure a combined concentration of both NO and $NO_2$ included in the sample gas, dilution block 220 may include a converter device, such as $NO_2$ converter 226, to convert $NO_2$ gas present in the diluted sample into NO gas. $NO_2$ converter 226 can include molybdenum metal, which when heated converts substantially all $NO_2$ gas present in the sample into NO gas. In an embodiment, $NO_2$ converter 226 can include pressed and/or sintered molybdenum metal powder formed into a porous filter element to increase the surface area of the metal and thereby improve the efficiency of the conversion process. The combination of nitrogen oxides such as NO and $NO_2$ can be referred to as NOx.

During operation, it is desirable to maintain the ratio of ozone gas, dilution gas, and sample gas substantially constant. However, the degree of restriction provided by ozone gas orifice 212, exhaust gas orifice 214, dilution gas orifice 222, and sample gas orifice 224 is determined, in part, by the temperature of each orifice and the temperature of the gases conducted therein. Accordingly, analysis block 210, dilution block 220, and the included orifices are maintained at a substantially constant operating temperature during operation of monitoring device 200. For example, monitoring device 200 can include one or more heating devices (not shown at FIG. 2). In an embodiment, a heating device can include a temperature regulation device to maintain the temperature of dilution block 220 at an elevated and substantially constant temperature during operation of monitoring device 200. In another embodiment, heat provided by the engine or equipment to which monitoring device 200 is incorporated can provide a suitable operating temperature. In still another embodiment, the operating temperature of analysis block 210 can be maintained at a substantially constant temperature using a thermo-electric cooling device.

Operating analysis block 210 and dilution block 220 at an elevated temperature also minimizes the condensation of water vapor within the chamber by decreasing the dew point of the diluted gases. In an embodiment, the preferred operating temperature of analysis block 210 is approximately 60° C., however the temperature may range from approximately 20° C. to approximately 200° C. The preferred operating temperature of dilution block 220 is approximately 120° C. when $NO_2$ converter 226 is not present, however the temperature may range from approximately 50° C. to approximately 450° C. The conversion efficiency of $NO_2$ converter 226 is substantially improved when it is operated at a temperature of approximately 300° C. and therefore the preferred operating temperature of dilution block 220 when $NO_2$ converter 226 is present is approximately 300° C.

Photon detector 216 can include a semiconductor photodiode, a photo-multiplier vacuum tube, or another type of photon detector. Photon detector 216 can be provided external to analysis block 210 by providing an air-tight and substantially transparent window to conduct light from reaction area 218 to photon detector 216. Photon emissions associated with chemiluminescence of the excited $NO_2$ gas occurs at a wavelength ranging approximately from 700 to 1500 nanometers. Signal noise provided by photon detector 216 can increase when photon detector 216 is operated at higher temperatures. Accordingly, photon detector 216 can be advantageously isolated thermally, to a desired degree, from analysis block 210.

Ozone generator 230 converts oxygen present in air or oxygen received from a compressed gas cylinder into ozone gas using high-voltage electrical corona, an ultra violet light source, or by another technique. As used herein, the term ozone gas refers to an ozone-containing gas, wherein the concentration of ozone in the ozone-containing gas is approximately 1%.

As previously described, suction 260 is applied to the outlet of analysis block 210 downstream from exhaust gas orifice 214. The suction can be provided by a vacuum pump, an eductor, or by another device. An eductor includes a venturi device operated by pressurized air, gas, or other fluid, and is preferable to a vacuum pump in so much as monitoring device 200 can be implemented without the use of moving mechanical components.

In the embodiment illustrated at FIG. 2, analysis block 210 and dilution block 220 are approximately contiguous and located within enclosure 240. Furthermore, monitoring device 200 can be mounted proximate to an exhaust conduit, such as exhaust conduit 10 of FIG. 1. Arranging the components in close proximity can be advantageous because a total volume of gas included internal to monitoring device 200 can be minimized thereby reducing a response time of monitoring device 200. Response time refers to how quickly monitoring device 200 can sample gas from exhaust conduit 10 and therefore how quickly monitoring device 200 can respond to a change in NOx concentration at exhaust conduit 10. A substantially fast response time is desirable when monitoring device 200 is included at a real-time closed-loop system such as a Selective Catalytic Reduction (SCR) reactor.

Figure 3:
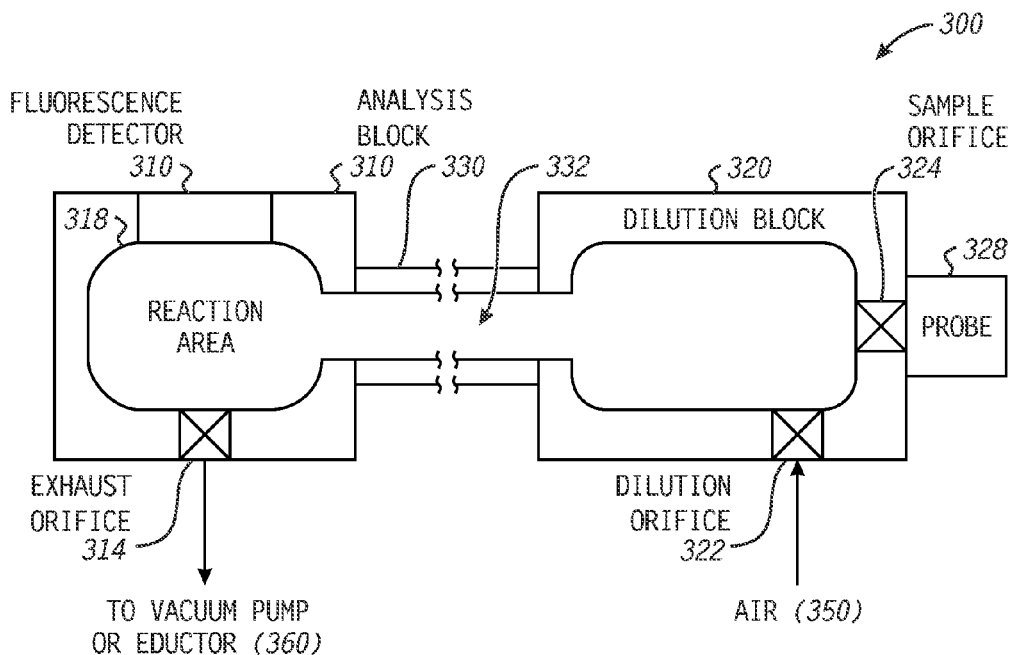
FIG. 3 is a schematic block diagram illustrating another example implementation of the monitoring device of FIG. 1 in accordance with a specific embodiment of the present disclosure.

FIG. 3 shows a monitoring device 300 in accordance with another embodiment of the present disclosure. Monitoring device 300 includes an analysis block 310, a dilution block 320, and a conduit 330. Analysis block 310 includes an exhaust gas orifice 314 and an ultra-violet fluorescence detector 316. Dilution block 320 includes a dilution gas orifice 322, a sample gas orifice 324, and a probe 328. Pressurized and metered dried air 350 is provided to dilution orifice 322. Suction 360 is applied at exhaust orifice 314. An enclosed chamber 332 is defined within the combined assembly of analysis block 310, dilution block 320, and conduit 330.

Monitoring device 300 is configured to determine a concentration of sulfur dioxide ($SO_2$) gas present in a sample gas collected by probe 328. Operation of monitoring device 300 is similar to the operation of monitoring device 200 of FIG. 2 with the exception that monitoring device 300 does not include an ozone gas orifice and associated ozone generator, and photon detector 216 is replaced with an ultra-violet fluorescence detector 316. Ultra-violet fluorescence detector 316 can include an ultra-violet light source and a photon detector. In an embodiment, the photon detector of fluorescence detector 316 can include a semiconductor photo-diode, a photo-multiplier vacuum tube, or another type of photon detector.

During operation, a sample of gas is extracted from a stream of gases communicated by a stack or duct, such as exhaust conduit 10 of FIG. 1, using probe 328. The sample gas enters dilution block 320 via sample gas orifice 324 and is substantially immediately diluted with a dilution gas received at dilution block 320 via dilution gas orifice 222. The diluted sample gas is conveyed to analysis block 310, via conduit 330, where it is extracted via exhaust orifice 314 in response to a suction device such as a vacuum pump or an eductor. Ultra-violet fluorescence detector 316 illuminates the diluted sample gas as it flows through reaction area 318 of analysis block 310 and detects fluorescence of $SO_2$ gas present in the diluted sample gas using a suitable photon detector. The intensity of the detected fluorescence can be used to determine a concentration of $SO_2$ gas present in the diluted sample gas, and ultimately to determine a concentration of $SO_2$ gas present in the exhaust gas stream at exhaust conduit 10.

Analysis block 310 and dilution block 320 are located remote from one another. The gas pressure throughout enclosed chamber 332 is substantially uniform so that a partial pressure of the dilution gas and a partial pressure of the sample gas within chamber 332 is maintained based on the amount of restriction provided by dilution gas orifice 322 and sample gas orifice 324, respectively. Heating devices (not shown at FIG. 3) can independently control the temperature of analysis block 310 and dilution block 320.

Figure 4:
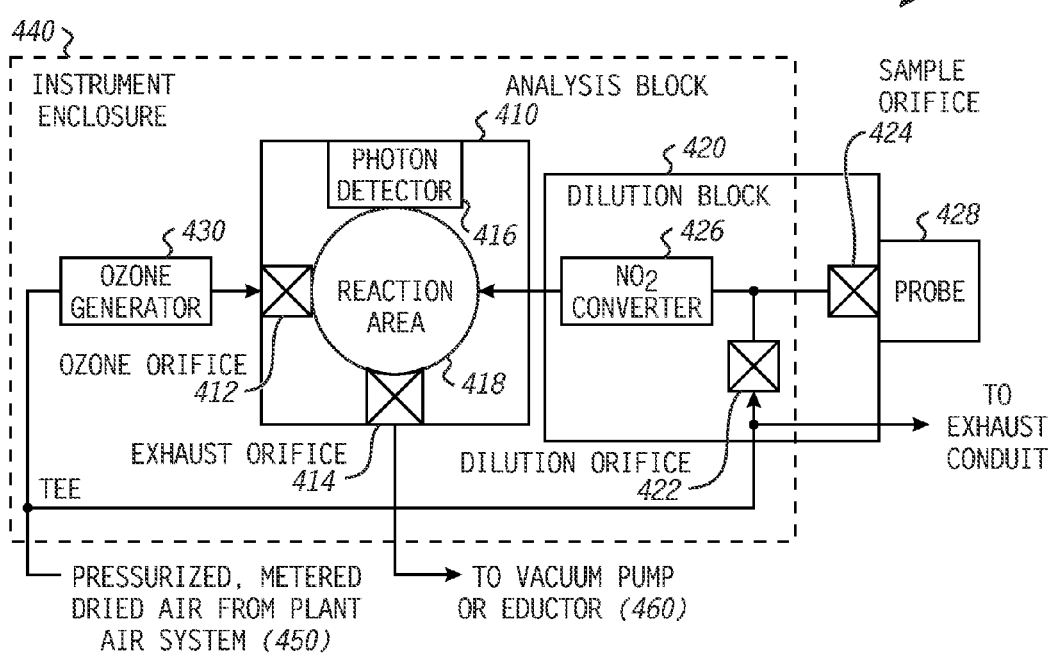
FIG. 4 is a schematic block diagram illustrating yet another example implementation of the monitoring device of FIG. 1 in accordance with a specific embodiment of the present disclosure.

FIG. 4 shows a monitoring device 400 in accordance with still another embodiment of the present disclosure. Monitoring device 400 is configured to measure a concentration of NOx present in a diluted sample, and includes an analysis block 410, a dilution block 420, and an ozone generator 430, included at an instrument enclosure 440. Analysis block 410 includes an ozone gas orifice 412, an exhaust gas orifice 414, a photon detector 416, and a reaction area 418. Dilution block 420 includes a dilution gas orifice 422, a sample gas orifice 424, a nitrogen dioxide ($NO_2$) converter 426, and a probe 428. Pressurized and metered dried air 450 is provided to ozone generator 430 and to dilution orifice 422. Suction 460 is applied at exhaust orifice 414.

Operation of monitoring device 400 is similar to the operation of monitoring device 200 of FIG. 2 except pressurized and metered air provided to ozone generator 430 and to dilution orifice 422 is overflowed and vented to the exhaust conduit from which probe 428 extracts the gas being sampled, such as exhaust conduit 10 of FIG. 1. Because the pressure of air supplied to ozone generator 430 and to dilution orifice 422 are referenced to the pressure within exhaust conduit 10, the relative flow of gases through ozone gas orifice 412, dilution gas orifice 422, and sample gas orifice 424, and therefore the ratio of these three gas sources within monitoring device 400, remains substantially constant despite fluctuations in pressure within exhaust conduit 10. In addition, referencing each of the three gas sources to the pressure within exhaust conduit 10 allows monitoring device 400 to compensate when the pressure within exhaust conduit 10 is significantly different that ambient pressure. In an embodiment, a pressure sensor (not shown at FIG. 4) can be included at analysis block 410 or at dilution block 420 to monitor the air pressure at the chamber included therein. During operation, monitoring device 400 can compensate for chamber pressure variations caused by variations in pressure within exhaust conduit 10 based on a characterized compensation equation.

Figure 5:
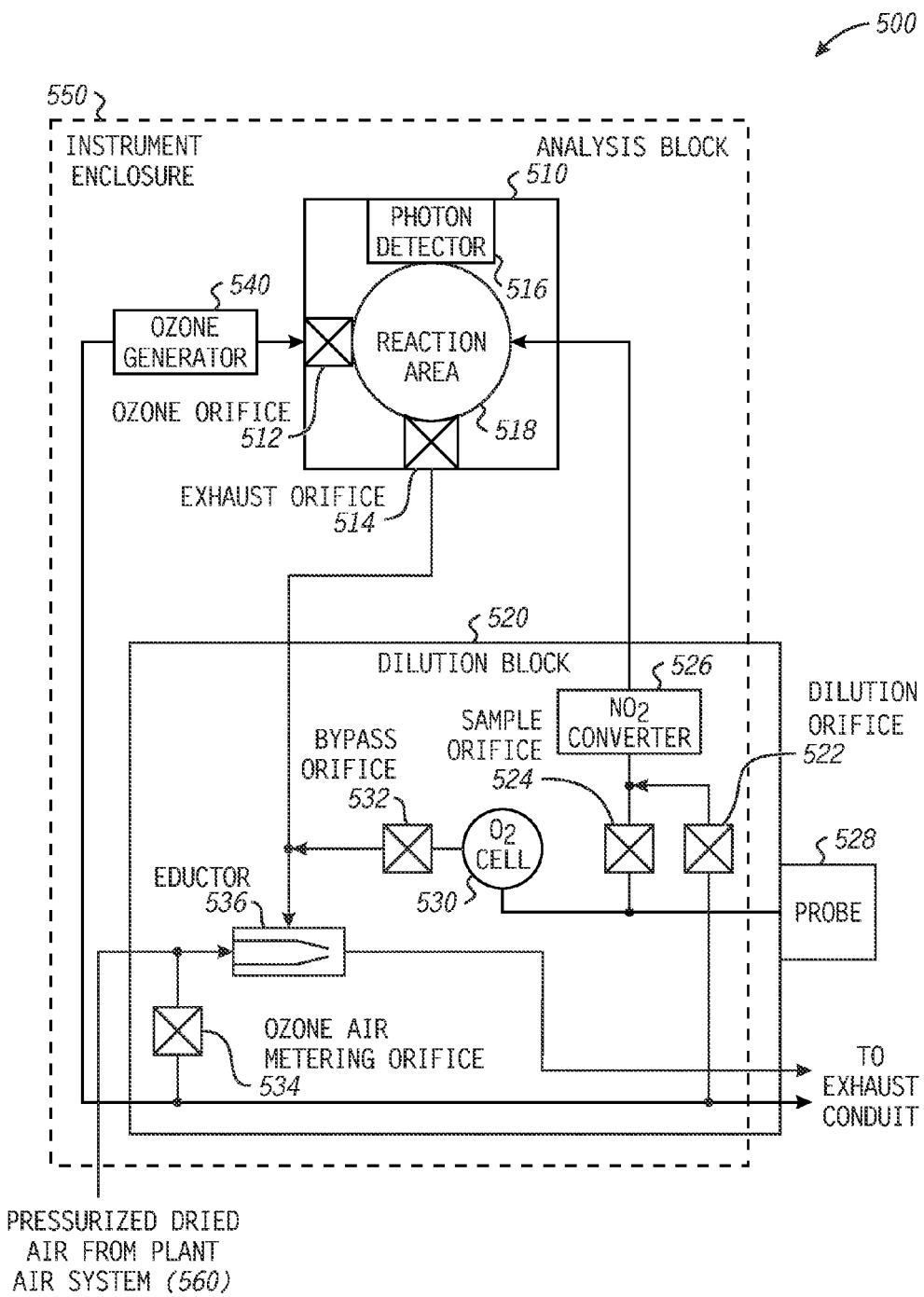
FIG. 5 is a schematic block diagram illustrating sill another example implementation of the monitoring device of FIG. 1 in accordance with a specific embodiment of the present disclosure.

FIG. 5 shows a monitoring device 500 in accordance with yet another embodiment of the present disclosure. Monitoring device 500 is configured to measure a concentration of NOx present in a diluted sample, and includes analysis block 510, dilution block 520, and ozone generator 540, included at an instrument enclosure 550. Analysis block 510 includes an ozone gas orifice 512, an exhaust gas orifice 514, a photon detector 516, and a reaction area 518. Dilution block 520 includes a dilution gas orifice 522, a $NO_2$ converter 526, a probe 528, an oxygen sensor 530, a bypass orifice 532, an ozone air metering orifice 534, and an eductor 536. Pressurized dried air 560 is provided to dilution block 520.

The operation of monitoring device 500 is similar to that described with reference to monitoring device 200 of FIG. 2 and monitoring device 400 of FIG. 4, but includes additional features. As previously described, a suction is applied at the outlet of analysis block 510 via exhaust orifice 514 to provide a reduced and substantially uniform pressure throughout an enclosed chamber defined within analysis block 510 (including reaction area 518) and portions of dilution block 520 adjacent to dilution gas orifice 522 and sample gas orifice 524. A sample gas is extracted from an exhaust conduit (not shown) via probe 528 and sample gas orifice 524. The sample gas is substantially immediately diluted with dilution gas (air in this example), and the diluted sample gas is passed through $NO_2$ converter 526 prior to entering reaction area 518 at analysis block 510. NO gas present in the converted and diluted sample gas reacts with ozone gas received via ozone orifice 512 and photon detector 516 detects photons associated with the resulting chemiluminescence. A desired ratio (partial pressure) of ozone gas, dilution gas, and sample gas is maintained within the chamber by a relative degree of restriction provided by the ozone orifice, the dilution orifice, and the sample gas orifice, respectively.

Monitoring device 500 also includes an integrated eductor for supplying suction at the exhaust outlet of analysis block 510. The eductor is powered by pressurized and dried air, which also provides air to ozone generator 540 and dilution orifice 522 via ozone air metering orifice 534. Air provided at the output of ozone air metering orifice 534 is also overflowed to exhaust conduit 10 to compensate for absolute and varying air pressure within exhaust conduit 10 as described with reference to monitoring device 400 of FIG. 4.

Oxygen sensor 530 is integrated within dilution block 520. Oxygen sensor 530 receives undiluted sample gas from probe 528, which is drawn thru oxygen sensor 530 by suction provided by eductor 536 via bypass orifice 532. Oxygen sensor 530 can include a zirconium oxide ($ZrO_2$) oxygen cell or another type of oxygen sensor. A measure of oxygen gas present in an exhaust stream, in conjunction with NOx levels, can be useful in many applications for which monitoring device 500 is employed. In addition, a relatively large flow of sample gas can be drawn through probe 528 via bypass orifice 532 to minimize the residence time of the sample gas in the probe and thus improve how quickly monitoring device 500 can respond to changes in byproduct levels. Furthermore, all sample gas extracted from exhaust conduit 10 is returned to the exhaust conduit via eductor 536 to simplify plumbing associated with monitoring device 500 and so that the extracted sample gas is not vented into the immediate environment.

Figure 6:
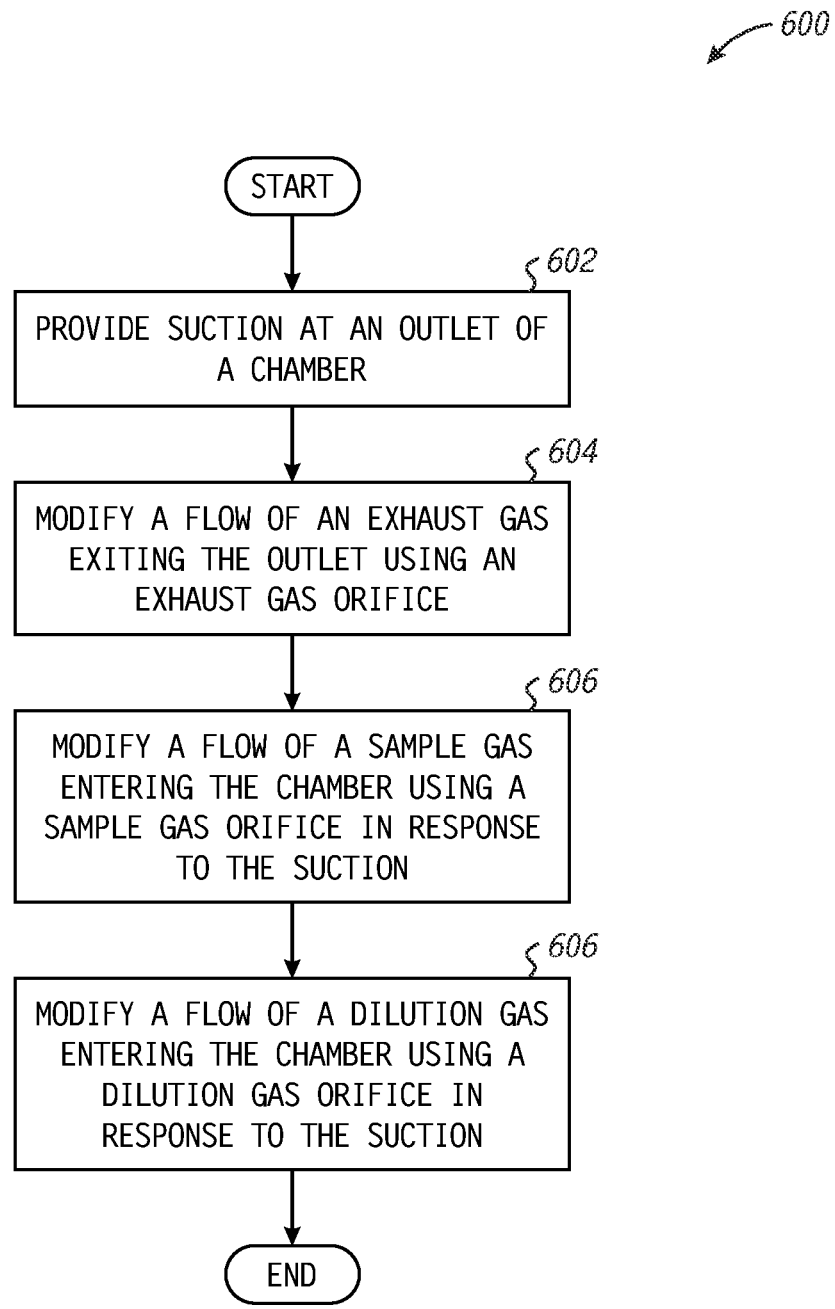
FIG. 6 is a flow diagram illustrating a method in accordance with a specific embodiment of the present disclosure.

FIG. 6 is a flow diagram illustrating a method 600 in accordance with a specific embodiment of the present disclosure. Method 600 illustrates a technique for controlling the ratio of a dilution gas to a sample gas at a monitoring device. The method begins at block 602 where suction is provided at an outlet of a chamber. For example, analysis block 210 and dilution block 220 of FIG. 2 together provide a chamber for diluting and subsequently analyzing a sample gas. The flow proceeds to block 604 where a flow of an exhaust gas exiting the outlet is modified using an exhaust gas orifice. For example, a bore diameter of exhaust gas orifice 214 at analysis block 210 of FIG. 2 is selected to control a total amount of gases entering and exiting the chamber. The flow proceeds to block 606 where a flow of a sample gas entering the chamber is modified using a sample gas orifice in response to the suction. For example, a bore diameter of sample gas orifice 224 at dilution block 220 of FIG. 2 is selected to control the rate at which a sample gas enters the chamber as it is drawn into the chamber by the suction applied at exhaust orifice 214. The flow proceeds to block 608 where a flow of a dilution gas entering the chamber is modified using a dilution gas orifice in response to the suction. For example, a bore diameter of dilution gas orifice 222 at dilution block 220 of FIG. 2 is selected to control the rate at which a dilution gas enters the chamber as it is drawn into the chamber by the suction applied at exhaust orifice 214.

The present disclosure describes a device and techniques for sampling gases present in an exhaust stream. The device includes a dilution block coupled to an analysis block, which together define an enclosed chamber. The dilution block includes an inlet for receiving a dilution gas via a dilution gas orifice and another inlet for receiving a sample gas from the exhaust stream via a sample gas orifice. Sample gas and dilution gas are drawn into the chamber at the dilution block in response to a suction provided at an outlet of the analysis block, the suction applied downstream from an exhaust orifice. In an embodiment, the analysis block includes an inlet for receiving ozone gas via an ozone gas orifice. A degree of restriction provided by the ozone gas orifice, the dilution gas orifice, and the sample gas orifice can be selected to determine a corresponding partial pressure of the ozone gas, the dilution gas, and the sample gas within the analysis block. In an embodiment, a photon detector is optically coupled to the interior of the analysis block for detecting chemiluminescence resulting from a reaction of ozone gas with nitric oxide (NO) gas present in the sample gas. The rate of photon emission can be used to determine a concentration of nitrogen oxide gases in the sampled exhaust stream.

Note that not all of the activities or elements described above in the general description are required, that a portion of a specific activity or device may not be required, and that one or more further activities may be performed, or elements included, in addition to those described. Still further, the order in which activities are listed are not necessarily the order in which they are performed.

Also, the concepts have been described with reference to specific embodiments. However, one of ordinary skill in the art appreciates that various modifications and changes can be made without departing from the scope of the present disclosure as set forth in the claims below. Accordingly, the specification and figures are to be regarded in an illustrative rather than a restrictive sense, and all such modifications are intended to be included within the scope of the present disclosure.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

What is claimed is:

1. A device comprising:
    an analysis block defining a first portion of a chamber;
    a dilution block defining a second portion of the chamber;
    a first orifice at the first portion for withdrawing gas from the chamber in response to a suction applied at the first orifice;
    a second orifice at the second portion to modify passage of a sample gas entering the chamber in response to the suction;
    a third orifice at the second portion to modify passage of a dilution gas entering the chamber in response to the suction; and
    a fourth orifice at the first portion to modify passage of ozone gas entering the chamber in response to the suction;
    wherein a partial pressure of the sample gas within the chamber, a partial pressure of the dilution gas within the chamber, and a partial pressure of the ozone gas within the chamber is maintained based only on a respective restriction provided by the second orifice, the third orifice, and the fourth orifice.

2. The device of claim 1 further comprising a suction device for providing the suction at the first orifice.

3. The device of claim 2 wherein the suction device includes an eductor.

4. The device of claim 1 further comprising a heating device to elevate a temperature of the analysis block or the dilution block.

5. The device of claim 1 wherein the dilution block further comprises a converter device for converting a portion of nitrogen dioxide gas present in the sample gas into nitric oxide gas, the converter comprising Molybdenum metal included within the chamber.

6. The device of claim 1 further comprising a photon detector optically coupled to the first portion of the chamber.

7. A method comprising:
providing a suction at an outlet of a first portion of a chamber, the first portion defined within an analysis block;
modifying a flow of an exhaust gas exiting the outlet, the flow determined by a first orifice included at the outlet;
modifying a flow of a sample gas entering a second portion of the chamber in response to the suction, the flow determined by a second orifice, and wherein the second portion is defined within a dilution block;
modifying a flow of a dilution gas entering the second portion of the chamber in response to the suction, the flow determined by a third orifice; and
modifying a flow of ozone gas entering the first portion of the chamber in response to the suction, the flow determined by a fourth orifice.

8. The method of claim 7 further comprising maintaining a desired partial pressure of the sample gas within the chamber, maintaining a desired partial pressure of the dilution gas within the chamber, and maintaining a desired partial pressure of the ozone gas within the chamber based only on a respective restriction provided by the second orifice, the third orifice, and the fourth orifice.

9. The method of claim 7 wherein providing the suction at the outlet comprises providing the suction using an eductor.

10. The method of claim 7 further comprising heating the analysis block or the dilution block.

11. The method of claim 7 further comprising converting a portion of nitrogen dioxide gas present in the sample gas into nitric oxide gas using Molybdenum metal included within the chamber.

12. The method of claim 7 further comprising detecting photon emissions resulting from chemiluminescence induced within the analysis block.

13. The method of claim 12 further comprising determining a concentration of nitric oxide gas present in the sample gas based on detecting the photon emissions.

14. A device comprising:
a housing operable to maintain a substantially uniform pressure at a chamber defined therein, the housing including:
an outlet for expelling an exhaust gas from the chamber in response to a suction applied to the outlet, the outlet including a first orifice operable to modify the flow of the exhaust gas exiting the chamber;
a first inlet for receiving a sample gas at the chamber in response to the suction, the first inlet including a second orifice operable to modify the flow of the sample gas into the chamber;
a second inlet for receiving a dilution gas at the chamber in response to the suction, the second inlet including a third orifice operable to modify the flow of the dilution gas into the chamber; and
a third inlet for receiving an ozone gas at the chamber in response to the suction, the third inlet including a fourth orifice operable to modify the flow of the ozone gas into the chamber;
wherein a partial pressure of the sample gas within the chamber, a partial pressure of the dilution gas within the chamber, and a partial pressure of the ozone gas within the chamber is determined only by an amount of restriction provided by each of the second orifice, the third orifice, and the fourth orifice.

15. The device of claim 14 further comprising an eductor operable to provide the suction at the outlet of the housing.

16. The device of claim 14 further comprising a photon detector optically coupled to the chamber.

* * * * *